United States Patent [19]

Buell

[11] Patent Number: 4,693,973

[45] Date of Patent: Sep. 15, 1987

[54] DNA SEQUENCES, RECOMBINANT DNA MOLECULES AND PROCESSES FOR PRODUCING BOVINE GROWTH HORMONE-LIKE POLYPEPTIDES IN HIGH YIELD

[75] Inventor: Gary N. Buell, Geneva, Switzerland

[73] Assignee: Biogen N.V., Curacao, Netherlands Antilles

[21] Appl. No.: 522,357

[22] Filed: Aug. 11, 1983

[30] Foreign Application Priority Data

Aug. 17, 1982 [GB] United Kingdom ................. 8223695

[51] Int. Cl.[4] ...................... C12P 21/00; C12N 15/00
[52] U.S. Cl. ................................. 435/68; 435/172.3; 530/399
[58] Field of Search ............................. 435/172.3, 68; 260/112.5 R, 112

[56] References Cited

U.S. PATENT DOCUMENTS

| | | | |
|---|---|---|---|
| 3,265,579 | 8/1966 | Daniels et al. | 167/74 |
| 3,308,027 | 3/1967 | Reusser | 167/74 |
| 3,664,925 | 5/1972 | Sonenberg et al. | 195/29 |
| 4,056,520 | 11/1977 | Sonenberg et al. | 260/112.5 R |
| 4,443,539 | 4/1984 | Fraser et al. | 435/68 |

FOREIGN PATENT DOCUMENTS

| | | |
|---|---|---|
| 0047600 | 3/1982 | European Pat. Off. |
| 0067026 | 12/1982 | European Pat. Off. |
| 0068646 | 1/1983 | European Pat. Off. |
| 75444 | 3/1983 | European Pat. Off. |
| 85220 | 8/1983 | European Pat. Off. |
| 2031434 | 4/1980 | United Kingdom |
| 1565190 | 4/1980 | United Kingdom |
| 2073245 | 10/1981 | United Kingdom |

OTHER PUBLICATIONS

A. E. Wilhelmi, "Chemistry of Growth Hormone", in *Handbook of Physiology*, Williams & Wilkins, ed., §7, vol. 4, pp. 59-78 (1974).

E. J. Turman, "Some Effects of Pituitary Anterior Growth Hormone on Swine", Thesis; Purdue University (Apr. 1953).

W. L. Miller et al., "Molecular Cloning of DNA Complementary to Bovine Growth Hormone mRNA", *J. Biol. Chem.*, 255, pp. 7521-7524 (1980).

M. Wallis, *FEBS Lett.*, 35, pp. 11-14 (1973).

L. T. Hunt and M. O. Dayhoff, in *Atlas of Protein Sequence and Structure* 1976, 5, Supp. 2, p. 139 (1976).

E. Keshet et al., "Cloning of Bovine Growth Hormone Gene and Its Expression in Bacteria", *Nucleic Acids Research*, 9, pp. 19-30 (1981).

V. R. Lingappa et al., "Nascent Prehormones Are Intermediates in the Biosynthesis of Authentic Bovine Pituitary Growth Hormone and Prolactin", *Proc. Natl. Acad. Sci. U.S.A.*, 74, pp. 2432-2436 (1977).

*Primary Examiner*—Blondel Hazel
*Attorney, Agent, or Firm*—James F. Haley, Jr.; Margaret A. Pierri

[57] ABSTRACT

DNA sequences, recombinant DNA molecules and processes for producing bovine growth hormone-like polypeptides in high yield and the novel polypeptides produced thereby. These polypeptides are useful in improving the rate of growth of and meat production and quality in cattle.

6 Claims, 6 Drawing Figures

```
GGGGGGGGGGGGGGGGGGGGGATGGCTGCAGGCCCCCGGACCTCCCTGGCTTTCGCCCTGCTCCTGCCTTGCCTGGACTCAGGTGGTGGGC   100
                     MetAlaAlaGlyProArgThrSerLeuLeuAlaPheAlaLeuLeuLeuCysLeuProTrpThrGlnValValGly
                     -25                              -20                      -10                  -1

GCCTTCCCAGCCATGTCCTTGTCCGGCCTGTTTGCCAACGCTGTGCTCCGGGCTCAGCACCTGGCTGACACCTTCAAAGAGTTTGAG      199
AlaPheProAlaMetSerLeuSerGlyLeuPheAlaAsnAlaValLeuArgAlaGlnHisLeuAlaAspThrPheLysGluPheGlu
+1 +2                        10                          20                         30

CGCACCTACATCCCGGAGGGACAGAGATACTCCATCCAGAACACCCAGGTTGCCTTCTGCTTCTCTGAAACCATCCCGGCCCCCACGGGCAAGAATGAG   298
ArgThrTyrIleProGluGlyGlnArgTyrSerIleGlnAsnThrGlnValAlaPheCysPheSerGluThrIleProAlaProThrGlyLysAsnGlu
                  40                       50                         60

GCCCAGCAGAAATCAGACTTGGAGCTGCTTCGCATCCAGTCGTGGCTTGGGCCCCTGCAGTTTCTCAGCAGAGTCTTCACCAAC          397
AlaGlnGlnLysSerAspLeuGluLeuLeuArgIleGlnSerTrpLeuGlyProLeuGlnPheLeuSerArgValPheThrAsn
                70                          80                         90
```

```
AGCTTGGTGTTTGGCACCTCGGACCGTGTCTATGAGAAGCTGAAGGACCTGGAGGAAGGCATCTTGGCCCTGATGCGGGAGGTGGAAGATGGCACCCCC    496
SerLeuValPheGlyThrSerAspArgValTyrGluLysLeuLysAspLeuGluGluGlyIleLeuAlaLeuMetArgGluValGluAspGlyThrPro
100                                        110                                        120                          130

CGGGCTGGGCAGATCCTCAAGCAGACCTATGACAAATTTGACACACAAACATGCGCAGTGACGACGGCTGCTCAAGAACTACGGTCTGCTCTCCTGCTTC    595
ArgAlaGlyGlnIleLeuLysGlnThrTyrAspLysPheAspThrGlnThrCysAlaValThrThrAlaLeuLysAsnTyrGlyLeuLeuSerCysPhe
                               140                                        150                                        160

CGGAAGGACCTGCATAAGACGGAGACGTACCTGAGGGTCATGAAGTGCCGCCGCTTCGGGGAGGCCAGCTGTGCCTTCTAGTTGCCAGCCATCTGTTGT    694
ArgLysAspLeuHisLysThrGluThrTyrLeuArgValMetLysCysArgArgPheGlyGluAlaSerCysAlaPheEM
                               170                                        180                    190 191

TTGCCCCTCCCCGTGCCTTCCTTGACCCTGGAAGGTGCCACTCCCCCCCCCCCCCCCCCCCCCCCC                                  765
```

DNA SEQUENCES, RECOMBINANT DNA MOLECULES AND PROCESSES FOR PRODUCING BOVINE GROWTH HORMONE-LIKE POLYPEPTIDES IN HIGH YIELD

TECHNICAL FIELD OF INVENTION

This invention relates to novel DNA sequences, recombinant DNA molecules and processes for producing bovine growth hormone-like polypeptides in high yield. More particularly, it relates to novel DNA sequences expressed in appropriate hosts in high yield and the novel bovine growth hormone-like polypeptides produced in those hosts. The DNA sequences and recombinant DNA molecules of this invention are characterized in that they code for novel polypeptides having the growth enhancing biological activity of bovine growth hormone. As will be appreciated from the disclosure to follow the DNA sequences, recombinant DNA molecules and processes of this invention may be used in the production of polypeptides useful as general anabolic agents in cattle, most especially to increase the rate of growth, weight gain and meat production in those animals.

BACKGROUND ART

Bovine growth hormone ("BGH") is a polypeptide hormone synthesized in and secreted from the anterior lobe of the pituitary. BGH is believed to be synthesized as a precursor protein (bovine pre-growth hormone) and to be matured to bovine growth hormone during secretion and release of the hormone into the blood stream. Moreover, it has been reported that protein fractions of natural bovine growth hormone include polypeptides that lack a number of amino-terminal amino acids, but which are still biologically active.

A nucleotide coding sequence and an amino acid sequence of bovine growth hormone have been reported [W. L. Miller et al., *J. Biol. Chem.*, 255, pp. 7521-24 (1980); L. J. Hunt and M. O. Dayhoff et al., in "Atlas Of Protein Sequence And Structure", Dayhoff ed., 5, Supp. 2, p. 139 (1976); M. Wallis, *FEBS Lett,* 35, pp. 11-14 (1973)]. It is a polypeptide of 191 amino acids and appears to be synthesized initially as a bovine pre-growth hormone of 217 amino acids; the signal sequence of 26 amino acids being removed from the N-terminal position during synthesis and secretion [V. R. Lingappa et al., *Proc. Natl. Acad. Sci. USA,* 74, pp. 2432-36 (1977)].

Growth hormones are normally produced throughout the life cycle, although apparently in higher amounts during the pre-adult period. These hormones are known to promote skeletal growth, nitrogen retention, protein synthesis and to affect glucose and lipid metabolism. Accordingly, growth hormones are recognized as general anabolic agents.

Growth hormones are somewhat species specific. However, a growth hormone from one species may be biologically active in another species lower in the evolutionary scale. Although the mechanism of growth hormone's activity is not well understood, it has been demonstrated that the administration of growth hormone markedly increases the rate of growth, weight gain, and meat production in animals. For example, in one test, the average rate of weight gain in pigs receiving daily injections of purified swine growth hormone was 2.26 pounds per day (as compared to an average weight gain of 2.19 lbs/day in control pigs). More importantly, the treated pigs consumed significantly less feed per day than the control pigs (7.03 lbs as compared to 8.40 lbs). In addition, the treated pigs displayed a marked improvement in carcass quality—the carcasses of the growth hormone-treated pigs averaged 30.57 inches in length and had 1.40 inches of backfat, while those of the control group averaged 29.33 inches in length and had 1.77 inches of backfat. The chemical composition of the edible meat was also markedly improved in the growth hormone-treated animals—13.50% protein, 49.14% moisture and 36.76% fat—as compared to the control group—10.8% protein, 39.43% moisture and 49.27% fat [E. J. Turman, "Some Effects Of Pituitary Anterior Growth Hormone On Swine", Thesis; Purdue University (April 1953)].

Unfortunately, the above-described improved growth and enhanced meat production in animals using growth hormone are not able to be widely realized in cattle because there is insufficient BGH available. Today, BGH is extracted from pituitary glands of cattle or produced via recombinant DNA technology in appropriate hosts, e.g., W. L. Miller et al., *Journal Biological Chem.,* 255, pp. 7521-24 (1980), European patent application 47,600 and United Kingdom patent application No. 2,073,245A. Plainly, the former source is not nearly adequate to provide the needed commercial quantities of BGH. The latter source is also not adequate because the expression yields of BGH in various hosts have been too low to provide economically-useful or commercial quantities of BGH.

DISCLOSURE OF THE INVENTION

The present invention solves the problems referred to by providing DNA sequences that code for novel BGH-like polypeptides and by expressing those sequences in high yields in appropriate hosts to produce efficiently and economically large quantities of polypeptides displaying the growth enhancing, biological activity of BGH. Accordingly, by virtue of this invention, it is for the first time possible to obtain polypeptides displaying the activity of BGH in commercial quantities for use in diverse applications to increase the rate of growth of and meat production in cattle.

As will be appreciated from the disclosure to follow, the novel DNA sequences and recombinant DNA molecules of this invention are capable of directing the production, in appropriate hosts, of large amounts of bovine growth hormone-like polypeptides, i.e., novel polypeptides displaying the growth-enhancing, biological activity of BGH. The novel polypeptides of this invention are useful, either as produced in the host or after further derivatization or modification, in compositions and methods for improving the growth rates of and meat production in cattle.

It will accordingly be appreciated from the foregoing that a basic aspect of this invention is the preparation of DNA sequences which code for polypeptides displaying the growth-enhancing biological activity of BGH, which are characterized by amino terminal deletions from the DNA sequence coding for mature bovine growth hormone, and which allow the production of such BGH-like products in at least about 100 times higher yield, and preferably at least about 1000 times higher yield, in appropriate hosts and expression vectors, than the DNA sequences coding for mature bovine growth hormone formerly employed for such expression. Such DNA sequences comprise, for example, DNA inserts selected from the group consisting of the DNA inserts of pBGH-Δ4, pBGH-Δ9, pBGH-Δ4(Ser), pBGH-Δ9(Ser), and other DNA inserts characterized by an amino terminal deletion from the DNA sequence coding for mature bovine growth hormone, said inserts allowing the production of a bovine growth hormone-like polypeptide in at least 100 times higher yield than the DNA sequence coding for mature bovine growth hormone.

BEST MODE OF CARRYING OUT THE INVENTION

In order that the invention herein described may be more fully understood, the following detailed description is set forth.

In the description the following terms are employed:

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose). That combination of a base and a sugar is called a nucleoside. Each nucleotide is characterized by its base. The four DNA bases are adenine ("A"), guanine ("G"), cytosine ("C") and thymine ("T"). The four RNA bases are A, G, C and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode for the amino acid leucine ("Leu"), TAG, TAA and TGA are translation stop signals and ATG is a translation start signal.

Reading Frame—The grouping of codons during translation of mRNA into amino acid sequences. During translation the proper reading frame must be maintained. For example, the sequence GCTGGTTGTAAG may be translated in three reading frames or phases, each of which affords a different amino acid sequence:

GCT GGT TGT AAG—Ala-Gly-Cys-Lys
G CTG GTT GTA AG—Leu-Val-Val
GC TGG TTG TAA G—Trp-Leu-(STOP)

Polypeptide—A linear array of amino acids connected one to the other by peptide bonds between the α-amino and carboxy groups of adjacent amino acids.

Genome—The entire DNA of a cell or a virus. It includes, inter alia, the genes coding for the polypeptides of the organism, as well as operator, promoter and ribosome binding and interaction sequences, including sequences such as the Shine-Dalgarno sequences.

Gene—A DNA sequence which encodes through its template or messenger RNA ("mRNA") a sequence of amino acids characteristic of a specific polypeptide.

Transcription—The process of producing mRNA from a gene.

Translation—The process of producing a polypeptide from mRNA.

Expression—The process undergone by a DNA sequence or gene to produce a polypeptide. It is a combination of transcription and translation.

Plasmid—A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance ($Tet^R$) transforms a cell previously sensitive to tetracycline into one which is resistant to it. A cell transformed by a plasmid is called a "transformant".

Phage or Bacteriophage—Bacterial virus many of which consist of DNA sequences encapsidated in a protein envelope or coat ("capsid").

Cloning Vehicle—A plasmid, phage DNA or other DNA sequence which is able to replicate in a host cell, which is characterized by one or a small number of endonuclease recognition sites at which such DNA sequences may be cut in a determinable fashion without attendant loss of an essential biological function of the DNA, e.g., replication, production of coat proteins or loss or promoter or binding sites, and which contains a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and have the capacity to infect some host cell and be maintained therein.

Expression Control Sequence—A sequence of nucleotides that controls and regulates expression of DNA sequences or genes when operatively linked to those sequences. They include the lac system, the trp system, major operator and promoter regions of phage λ, the control region of fd coat protein and other sequences known to control the expression of genes of prokaryotic or eukaryotic cells and their viruses or combinations thereof.

BGH—Bovine growth hormone.

BGH-Like Polypeptide—A polypeptide displaying the growth-enhancing biological activity of BGH.

PREPARATION OF A RECOMBINANT DNA MOLECULE HAVING A DNA SEQUENCE CODING FOR BOVINE GROWTH HORMONE

Figure 1:
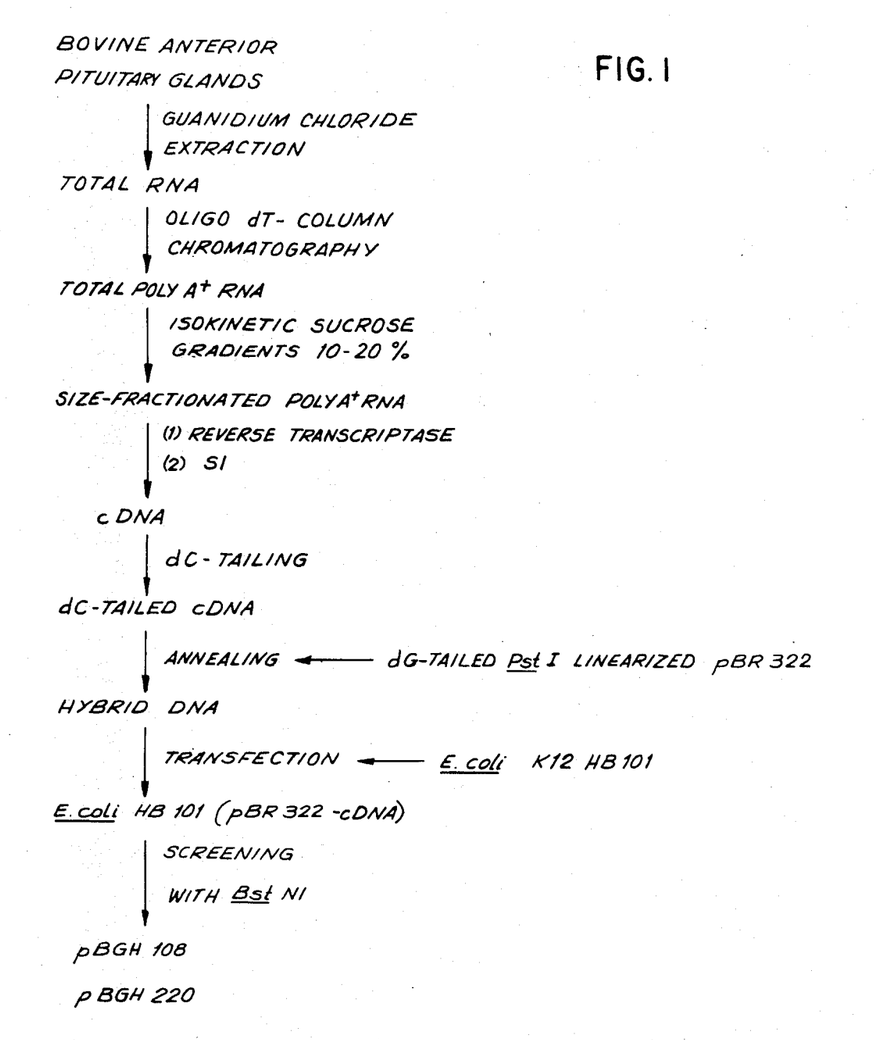
FIG. 1 is a schematic outline of one embodiment of a method for preparing a recombinant DNA molecule characterized by a DNA sequence encoding BGH.

Referring now to FIG. 1, we have shown therein a schematic outline of one embodiment of a process for preparing a recombinant DNA molecule characterized in that it has a DNA sequence coding for bovine growth hormone.

We isolated the RNA encoding bovine growth hormone from bovine pituitary glands by extracting the tissue with guanidium chloride and chromatographing the extract on an oligo dT-column [H. Goodman and R. MacDonald, in *Methods in Enzymology Recombinant DNA*, R. Wu, ed., 68, pp. 75-89 (1979); H. Aviv and P. Leder, *Proc. Natl. Acad. Sci. USA*, 69, pp. 1408-12 (1972)]. We then size fractionated the resulting poly A+ RNA on isokinetic sucrose gradients (10-20%) [Buell et al., *J. Biol. Chem.* 253, pp. 2471-82 (1978); Wickens et al., *J. Biol. Chem.*, 253, pp. 2483-95 (1978)].

We employed the size fractionated poly A+ RNA containing message encoding bovine growth hormone [determined by rabbit reticulocyte cell-free translation system assay [H. Pelham and R. Jackson, *Eur. J. Biochem.*, 67, pp. 247 (1976)]] as a template for reverse transcription to prepare single-stranded cDNA and to double strand that cDNA, substantially as described in Buell, supra, and Wickens, supra.

After treatment of the double-stranded cDNA with S1 nuclease to open the hairpin structure, we added dC tails to the cDNA with terminal transferase [R. Roychoudhary et al., *Nucleic Acids Research*, 3, pp. 101-16 (1976)]. We then inserted the dC-tailed cDNA into a PstI linearized, dG-tailed PBR322 and transformed *E. coli* K12 HB101 with the recircularized recombinant DNA molecule [Küpper et al., *Nature*, 281, pp. 555-59 (1981); Buell et al., *J. Biol. Chem.*, 254, pp. 9277-83 (1979)].

To select those clones having a BGH-related DNA insert, we screened our library of clones [grown on media containing 15 μg/ml tetracycline] with the restriction endonuclease BstN1, using standard restriction conditions and buffers. Since the DNA sequence reported for BGH contains a unique BstN1 site, this screening method enabled us to select two clones containing long BGH-related sequences from the many other clones in our library that did not contain such sequences. We designated the recombinant DNA molecules of the two clones that we selected pBGH 108 and pBGH 220.

We isolated pBGH 108 in large quantity [R. D. Klein et al., *Plasmid*, 3, pp. 88-91 (1980)] and determined its nucleotide sequence [Maxam and Gilbert, *Proc. Natl. Acad. Sci. USA*, 74, pp. 560-64 (1977)]. We have depicted that sequence, and its corresponding amino acid sequence in FIG. 2. Our amino acid sequence agrees with that previously reported for BGH [Dayhoff, supra; Wallis, supra] except at amino acids 47 and 66. Our nucleotide sequence agrees with that previously reported for DNA encoding BGH [Miller, supra] except at positions 177, 240 and 454. The differences of position 177 and 240 do not result in an amino acid change, while the difference at 454 does result in an amino acid change. This latter change is consistent with the previously reported heterogeneity at this position [Wallis, supra].

Figure 2:
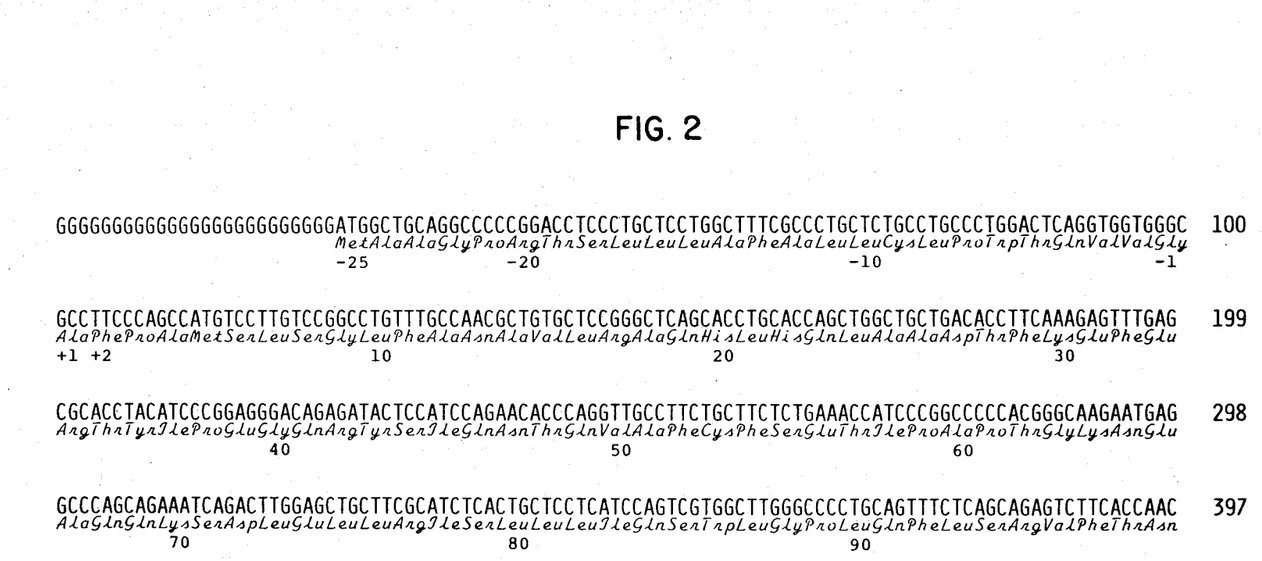
FIGS. 2 and 3 display the nucleotide sequence of a DNA insert encoding bovine pre-growth hormone, numbered from the end of the dG tail to the beginning of the dC tail (Nucleotides 1–713). The sequence depicted includes 25 of the 26 amino acids of the putative bovine pre-growth hormone signal sequence (numbered amino acids −25 to −1) and 191 of the amino acids of mature bovine growth hormone (numbered amino acids 1–191).
Figure 3:
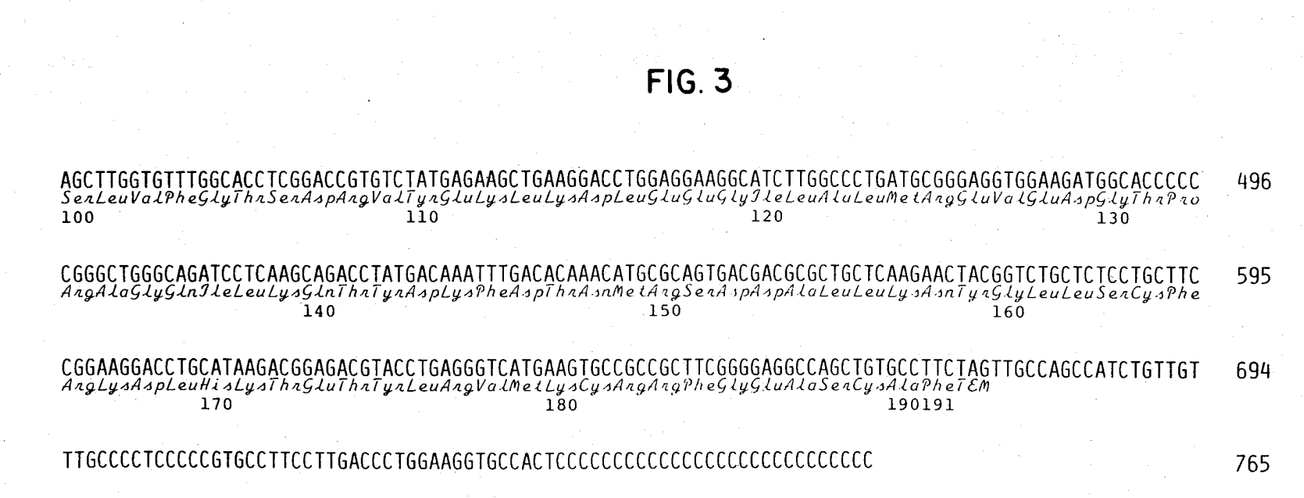

As shown in FIGS. 2 and 3, the DNA sequence of the insert of pBGH 108 encodes 25 of the 26 amino acids of the presumed signal sequence of bovine pre-growth hormone and the 191 amino acids of bovine growth hormone. The DNA sequence also contains 65 nucleotides from the 3' untranslated end of BGH (FIG. 3).

EXPRESSION OF A DNA SEQUENCE CODING FOR BOVINE GROWTH HORMONE

Using pBGH 108, we isolated the DNA sequence encoding the 191 amino acids of bovine growth hormone and constructed various expression vectors having that sequence fused directly to an ATG translation start signal and under the control of various expression control sequences to assay the level of synthesis of f-met-BGH (the 191 amino acids of BGH with a methionine at its amino terminus) in various *E. coli* host strains.

The results of those constructions and syntheses are depicted below:

| Promoter | Yield of BGH Activity (mg/l) | BGH-Like Molecules/cell |
| --- | --- | --- |
| trp | 0.001 | 50 |
| $P_L$ | 0.01 | ~1000 |

From these yields, we concluded that constructions that merely place an ATG start codon at the beginning of the DNA sequence coding for mature bovine growth hormone do not permit the synthesis of useful amounts of BGH in *E. coli*.

We also constructed various expression vectors having 5 amino acids of bovine pre-growth hormone (amino acids −1 to −5 in FIG. 2) between the ATG start codon and the GCC encoding the first amino acid (Ala) of mature bovine growth hormone. These constructions should result in the synthesis of a product having the 191 amino acids of BGH with 6 amino acids fused to its amino terminus (methionine plus the 5 amino acids from the pre-sequence of BGH).

The results of those constructions and syntheses are depicted below:

| Promoter | Yield of BGH Activity (mg/l) | BGH-Like Molecules/cell |
| --- | --- | --- |
| trp | 0.01 | 500 |
| $P_L$ | 0.01 | 1000 |

From these results we concluded that merely changing the distance between the expression control sequence of the particular construction and the ATG start codon does not appreciably improve the level of expression. We also concluded that varying the distance between the start codon and the first amino acid of mature bovine growth hormone does not help.

We than made a number of modifications in the $P_L$ controlled constructions, described above, to shorten the distance between the BGH coding sequence and the Shine Dalgarno sequence in the expression vector, to increase the promoter efficiency by deletions in the 99 nucleotide fragment carrying the Shine Dalgarno sequence (mu) of the vector, to remove the untranslated 3' dC end of the BGH coding sequences and to increase the plasmid copy number of the transformed hosts. However, none of these changes affected significantly the level of expression of BGH in hosts transformed with those vectors. It therefore appears that the BGH coding sequence has some inherent characteristics that prevent its high level expression in *E. coli*. *

*The low levels of observed synthesis cannot be explained by degradation of BGH in *E. coli*, because natural BGH appears to be stable in *E. coli* cell extracts.

While not wishing to be bound by theory, we believe that the low levels of expression of the BGH coding sequences in these vectors are caused by the binding of the A/G-rich sequences around and including the Shine-Dalgarno sequences (mu or trp) of the vectors and the T/C-rich areas at the beginning of the coding sequence for mature BGH. E.g.:

| | |
|---|---|
| mu site | AACTTAGGAGGGTTTTT |
| trp site | ACGTAAAAAGGGTATCG |
| BGH | ATG GCCTTCCCA GCC ATG TCC TTG TCC |

Such binding may obscure the ATG start codon and also prevent good binding of the ribosomes to the appropriate sequences.** Accordingly, we proposed to alter those T/C-rich areas at the beginning of the BGH coding sequence and thus to interfere with any binding to the required A/G-rich areas of the Shine-Dalgarno sequence.

**As further support for our theory, we have observed high levels of BGH-like polypeptide expression when the BGH coding sequence is fused to a DNA sequence coding for 99 amino acids from MS2 so as to be expressed as a fused protein. However, such fused protein is not preferred for cattle treatment because the extra amino acids carried by it may induce an immunogenic reaction in the treated animals.

One method to affect the T/C-rich areas of the BGH coding sequence would be to employ point mutations in the early codons of the BGH coding sequence so as to modify the T/C-rich regions but to preserve the amino acids coded for by those regions. However, a review of the early amino acids of BGH and the degenerate codons coding for them reveals that the T/C content of the early codons cannot be significantly affected by such amino acid preserving mutations. Accordingly, we decided to delete some of the codons in this T/C rich area of the BGH coding sequence.

CONSTRUCTION OF NOVEL DNA SEQUENCES ALLOWING THE PRODUCTION OF BGH-LIKE POLYPEPTIDES IN HIGH YIELD

Figure 4:
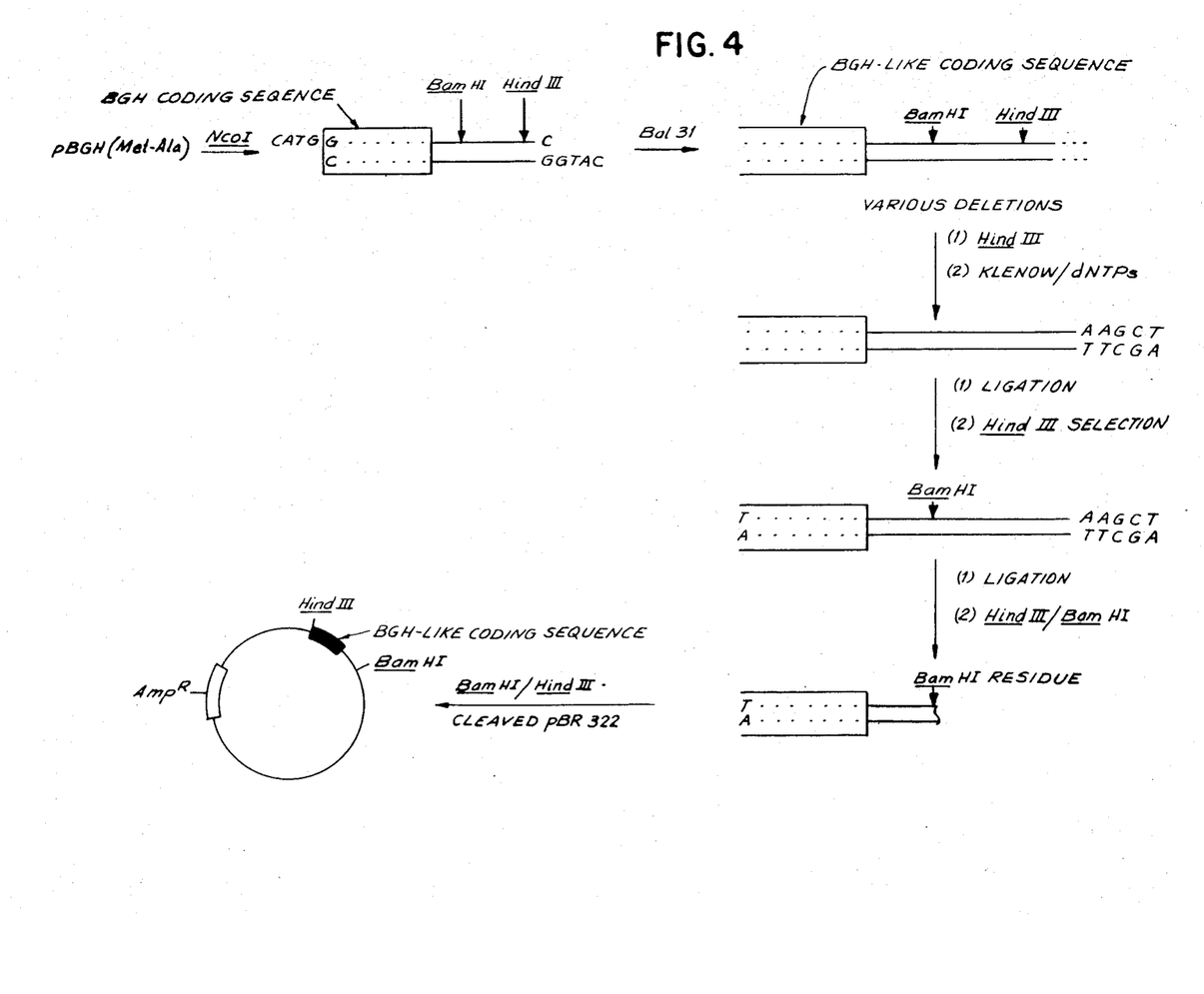
FIG. 4 displays one embodiment of a process of preparing a DNA sequence of this invention having a deletion in the amino terminal coding end of the bovine growth hormone coding region.

Referring now to FIG. 4, we have depicted therein one embodiment of a process for constructing DNA sequences of this invention allowing the production of novel BGH-like polypeptides in high yield in appropriate hosts.

We digested 10 μg pBGH-(Met-Ala) with NcoI (12 units) in 10×HindIII buffer and 100 μm NaCl at 37° C. for 60 min. We stopped the reaction by adding 5 μl EDTA (0.25M) and 1 μl ribonuclease. After heating the mixture at 37° C. for 5 min, we added 1 drop of phenol and shook the mixture. We then purified the linearized DNA by chromatography on A5M (Biorad) (elution with 10 mM Tris-HCl (pH 8), 1 mM EDTA) and pooled the DNA-containing peaks (400 μl). We then added 100 μl Bal 31 salts and 1 unit of Bal 31 and incubated the mixture at 30° C. to form deletions in the linearized DNA, substantially as described by N. Panayotatos and K. Truong, "Specific Deletion Of DNA Sequences Between Pre-selected Bases", *Nucleic Acids Research*, 9, pp. 5679–88 (1981). We took 100 μl aliquots from the mixture at five time points (10 sec, 20 sec, 30 sec, 45 sec and 60 sec) in order to generate various classes of deletions from the linearized DNA.

We quenched the deletion reaction in each aliquot by adding phenol and extracted the mixture once with 250 μl phenol and once with 0.5 μl ether. We precipitated the DNA with EtOH and collected it by centrifugation (8000 rpm, 8 min). Yield: ~10 μg in each aliquot.

Since the NcoI restriction site (CCATGG) in pBGH-(Met-Ala) is located near to the start of the DNA sequence encoding f-met BGH in that plasmid (FIG. 4), restriction with NcoI and treatment of the linearized DNA with Bal 31 will generate various deletions in the DNA sequence encoding BGH and therefore will produce DNA sequences that encode BGH-like polypeptides that lack one or more amino terminal amino acids, as compared to authentic BGH (FIG. 4).

In order to select those deletions ending with a T (chosen because of the convenient location of a HindIII site outside of the BGH coding sequence as described below), we employed the method described by N. Panayotatos and K. Truong, supra. We dissolved the DNA in 34 μl H₂O, added 4 μl 10×HindIII buffer and 20 units Hind III and incubated the mixture at 37° C. for 1 h. This restriction reaction cut the non-BGH end of the linearized DNA at the HindIII site (FIG. 4). We then filled in the HindIII site by mixing the DNA with 5 μl 1 mM dNTP's, 1 μl Klenow (1 unit) and incubated the mixture at 37° C. for 15 min. After fractionating the filled-in DNA on an agarose gel, we observed two bands: a small 100 base pair band corresponding to the minor HindIII fragment of the DNA and a large band corresponding to the major DNA fragment (shown in FIG. 4).

We eluted the major DNA fragment from the gel, precipitated it with EtOH and collected the DNA by centrifugation (8000 rpm, 8 min). As depicted in FIG. 4, this DNA fragment carries at one end a filled in HindIII restriction site (AAGCT) and at the other end one of the various deletions in the BGH coding sequence produced by the previously described Bal 31 digestion. Plainly, recircularization of the DNA will regenerate a HindIII site (AAGCTT) at the point of religation only in those cases where the Bal 31 deletion in the BGH coding sequence terminates with a T. Therefore, we religated the DNA and cleaved it again with HindIII to select the desired T-ending deletions (FIG. 4).

To recirculate the DNA, we dissolved the EtOH precipitate from above in 33 μl H₂O, combined that solution with 4 μl 10×ligation salts and 2 μl T4 DNA ligase and incubated the mixture at 14° C. for 16 h, substantially as described by [N. Panayotatos and K. Truong, supra]. We then stopped the reaction by heating the mixture at 70° C. for 15 min and isolated the DNA as before.

To isolate the DNA fragments carrying the desired deletions (i.e., those terminating in a T), we restricted the recircularized DNA from above with HindIII and BamHI. As depicted in FIG. 4, such restriction allows selection of a DNA fragment containing the deleted BGH coding sequence. Accordingly, we dissolved the DNA in 5 μl 10×HindIII buffer, added 20 units HindIII and 20 units BamHI and incubated the mixture at 37° C. for 60 min. After digestion we fractionated the mixture on an acrylamide gel and eluted the ~665 base pair fragment of desired DNA from the gel, precipitated it with EtOH and collected it by centrifugation as before. This fragment (in one strand) carries at one end the T marking the end of the particular deletion that we effected in the BGH coding sequence with Bal 31 digestion and at the other end the Bam HI cleavage residue which is located beyond the COOH-terminal end of the BGH coding sequence. In order to determine the nucleotide sequence of the various deletions (i.e. at which T the deletion stopped), we inserted our Bam HI-HindIII fragment in Hind III-Bam HI-linearized pBR322 by dissolving the DNA in 10 μl H₂O, adding 0.1 μg Hind III-Bam HI digested pBR322 (1 μl), 1.2 μl 10×ligation buffer and 0.5 ul T4 DNA ligase and incubated the mixture at 14° C. for 16 h.

After stopping the ligation, we transformed 200 μl of competent *E. coli* K12 λ (a gift of Walter Fiers) in the presence of 10 μl 0.1M MgCl₂ by chilling the cells in ice for 15 min, incubating them at 42° C. for 2 min and incubating them at room temperature for 10 min. After adding 2 ml L-Broth, we grew the cells at 37° C. for 1 h and plated a 200 μl aliquot onto petri plates, containing L-Broth supplemented with 50 μg/ml ampicillin. We grew our colonies at 37° C. for 16 h and randomly selected 24 clones from those colonies resistant to ampicillin.

We grew up cultures of each of these clones in 5 ml of L-Broth, we supplemented with 50 μg/ml ampicillin for 12 h at 37° C. and purified plasmid DNA from 1 ml of cells from each culture by the miniprep method described by [Klein et al., supra]. We then sized the Hind III-Bam HI inserts in the 24 plasmid DNAs by Hind III-Bam HI restriction and polyacrylamide gel fractionation. We selected 9 plasmid DNAs that had long inserts and sequenced some of the inserts by isolating the Hind III-Pst I fragment and employing the sequencing method described by Maxam and Gilbert, supra. Sequencing revealed that one of the inserts began at nucleotide 127(T) in FIG. 2 (i.e., the coding region for amino acids 1-9 of BGH had been deleted) and that another of the inserts began at nucleotide 112(T) in FIG. 2 (i.e., the coding region for amino acids 1-4 of BGH had been deleted).

EXPRESSION OF DNA SEQUENCES ALLOWING THE PRODUCTION OF NOVEL BGH-LIKE POLYPEPTIDES IN HIGH YIELD

Figure 5:
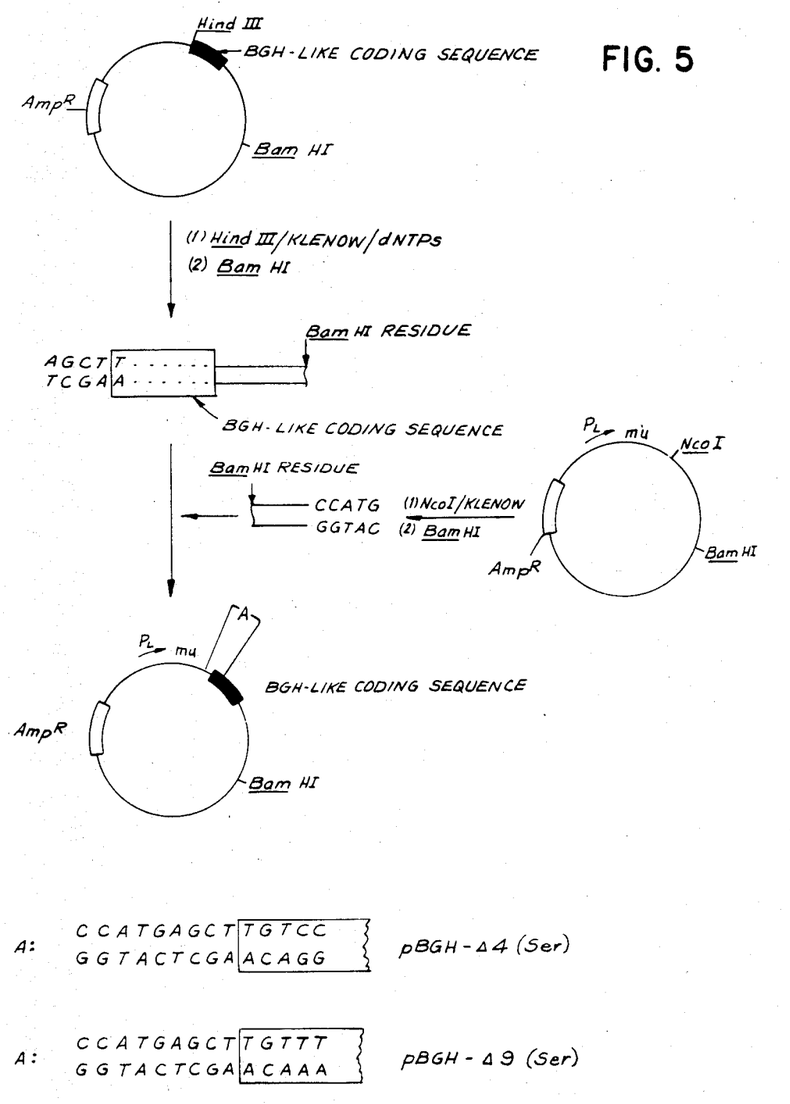
FIG. 5 displays one embodiment of a process of preparing expression vectors of this invention characterized by DNA sequences that permit high level expression of the novel bovine growth hormone-like polypeptides of this invention.

Referring now to FIG. 5, we have depicted therein one embodiment of a process for constructing an expression vector characterized by a DNA sequence of this invention that allows the production of novel BGH-like polypeptides in high yield.

To attempt to express DNA sequences from the two classes of deletions described above (Δ4 and Δ9), we isolated the DNA inserts from the plasmid DNA by cleaving the plasmid with Hind III, as before, filling in the Hind III fragment with Klenow as before, and then cleaving the DNA with 10 units of Bam HI under the conditions described previously. We then purified the desired BGH-related DNA fragment on a 5% (by weight) polyacrylamide gel. This fragment carries in one strand at its BGH-related end the sequence AGCTT, the AGCT coming from the filling in of the Hind III site and the final T being either nucleotide 104 of FIG. 2 (Δ9) or nucleotide 89 of FIG. 2 (Δ4).

To prepare our expression vector to receive this DNA sequence, we cleaved the identical vector that we had previously employed to express BGH sequences under the control of the P$_L$ promoter (e.g., pBGH-(Met-Ala)) with Nco I, filled in the fragment with Klenow and cleaved the linearized DNA with Bam HI using conventional conditions and buffers. This fragment carries in one strand at one end the sequence CCATG from the filling in of the Nco I site and at the other end the residue from the Bam HI cleavage (FIG. 5). We then combined 0.2 μg of the prepared vector (2 μl) and 0.5 μg of the prepared DNA in 1 μl of ligation buffer and 0.5 μl T4 DNA ligase and incubated them at 14° C. for 16 h.

This recircularization produced two vectors, respectively. In one the nucleotide sequence beginning with the ATG is ATGAGCTTG followed by amino acid 6 of the BGH coding sequence of FIG. 2 (pBGH-Δ4(Ser)) (FIG. 5). In the other the nucleotide sequence beginning with the ATG is ATGAGCTTG followed by amino acid 11 of BGH coding sequence of FIG. 2 (pBGH-Δ9(Ser)) (FIG. 5). Therefore, in the first construction, the coding region for the first four amino acids of mature BGH has been removed, the codon AGC (serine) inserted and the coding region for the fifth amino acid of mature BGH modified from ATG to TTG changing its amino acid from methionine to leucine. In the other construction, a preferred construction of this invention, the coding region for the first nine amino acids of mature BGH has been removed, the codon AGC (serine) inserted and the coding region for the tenth amino acid of mature BGH modified from CTG to TTG, a change that does not affect its amino acid (leucine). Therefore, the first construction should express a protein of the following sequence Met-Ser-Leu-amino acids 6-191 of mature BGH and the other construction should express a protein of the following sequence Met-Ser-amino acids 10-191 of mature BGH.*

Accordingly, we have designated these two vectors pBGH-Δ4(Ser) and pBGH-Δ9(Ser) (FIG. 5), respectively.

*Of course, it should be understood that the f-met may be removed from these polypeptides either during expression or subsequent thereto to produce polypeptides of the formula Ser-Leu-AA₆ to AA₁₉₁ of BGH and Ser-AA₁₀ to AA₁₉₁ of BGH, respectively. In fact, subsequent amino acid sequencing of BGH-Δ9(Ser) revealed that the f-met was cleaved either during expression or purification.

We employed the recircularized plasmids to transform *E. coli* K12 λ, as described before, again selecting those colonies that were resistant to ampicillin. We then grew up cultures of 12 of the ampicillin resistant clones, isolated their plasmid DNA by the miniprep method, described previously, and sized the inserts by Pst I/Eco RI restriction using conventional conditions. From the results of the sizing, we selected that plasmid DNA having the appropriate insert. We then used this DNA to transform *E. coli* MC 1061, substantially as described in G. N. Buell et al., *J. Biol. Chem.* 254, pp. 9729-83 (1979). We also transformed the cells with pcI857 (a gift of W. Friers).* We selected cells transformed with our BGH-related plasmid DNA and pcI857 by growing the colonies for 16 h at 30° C. in L-Broth, supplemented with ampicillin, as before, and kanamycin (40 μg/ml).

*pcI857 is a small plasmid that carries a temperature-sensitive P$_L$ repressor and the gene coding for kanamycin resistance.

We then randomly picked ampicillin and kanamycin-resistant colonies and grew them overnight in 5 ml L-Broth, supplemented as before with ampicillin and kanamycin, at 30° C. We diluted the cultures with 25 ml of L-Broth at 42° C. and allowed the cells to grow at 42° C. for 2 h (O.D.=1).**

**These are the identical growth conditions employed previously for P$_L$-controlled expression of BGH using the DNA sequence coding for mature BGH.

To isolate the BGH-like polypeptides produced by the transformed cells, we took 1 ml of cells and spun them down (8000 rpm, 4 min) added 50 μl Laemmli buffer (1% SDS) [Laemmli, *Nature,* 227, pp. 681 et seq. (1970)], boiled the mixture for 15 min, and again centrifuged the cells (8000 rpm, 4 min) to remove the cellular debris. We assayed the supernatant by radioimmunoassay for BGH using rabbit antisera to authentic BGH.***

***This is the identical isolation method and assay previously employed for $P_L$-controlled expression of BGH using the DNA sequence coding for mature BGH.

We obtained the following expression levels of BGH-like polypeptides:

| Deletion | Activity (mg/l) | BGH-like Molecules/cell |
|---|---|---|
| Δ4(Ser) | 30.0 | $1.5 \times 10^6$ |
| Δ9(Ser) | 100 | $5.0 \times 10^6$ |

We also used the Δ4(Ser) and Δ9(Ser) DNA sequences in the trp-containing vector previously used to express BGH using the DNA sequence coding for mature BGH. In those constructions, we obtained the following expression levels:

| Deletion | Yield of BGH Activity (mg/l) | BGH-like Molecules/cell |
|---|---|---|
| Δ4(Ser) | 0.15 | 8000 |
| Δ9(Ser) | 0.50 | 50000 |

Figure 6:
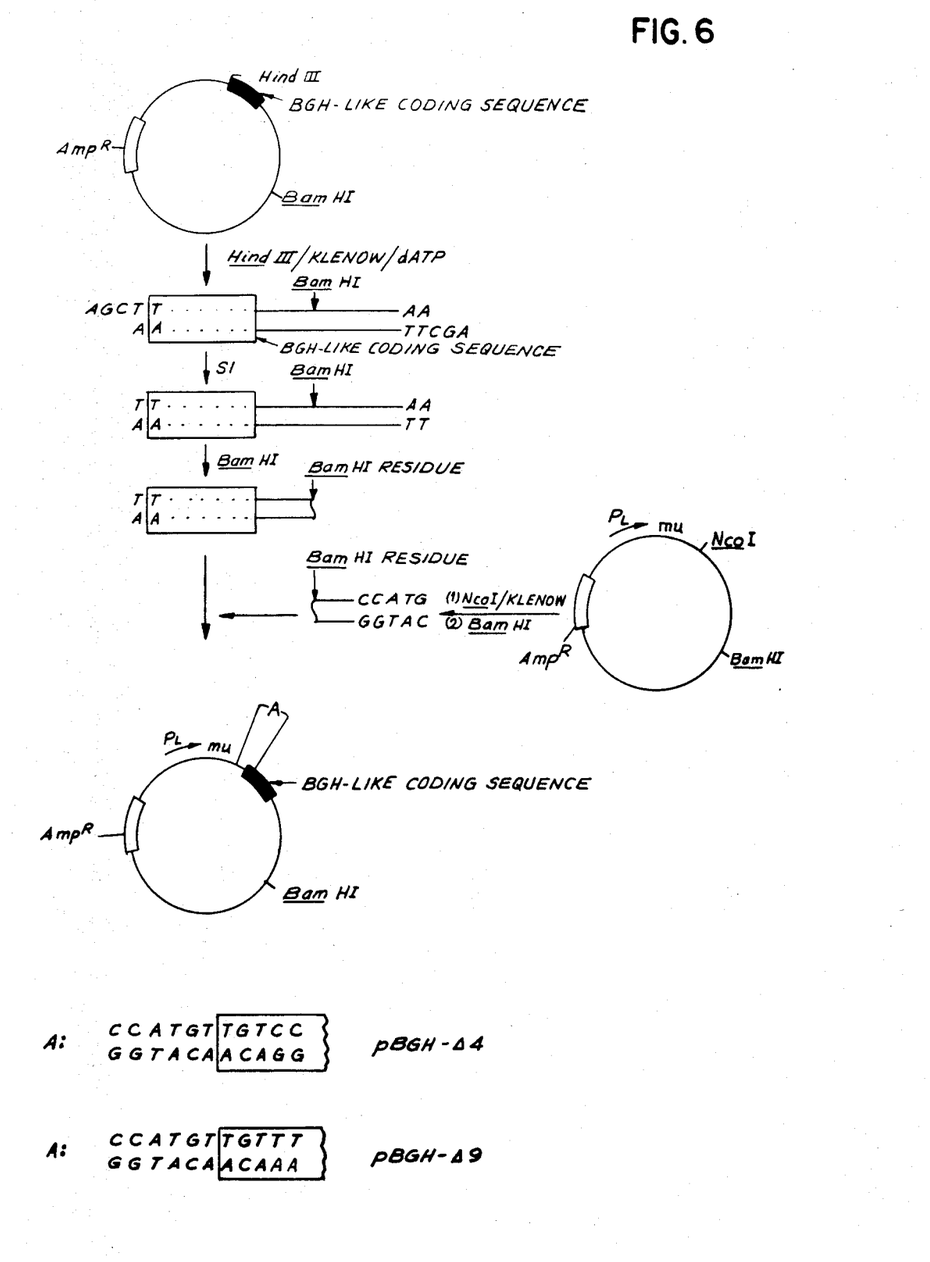
FIG. 6 displays another embodiment of a process of this invention for preparing expression vectors of this invention characterized by DNA sequences that permit high level expression of the novel bovine growth hormone-like polypeptides of this invention.

Finally, we manipulated our constructions to delete from the constructions the AGC codon (coding for serine) that had been added by the Hind III fill-in. The AGC deleted constructions pBGH-Δ4 and pBGH-Δ9 are the more preferred constructions of our invention, with pBGH-Δ9 being the most preferred.* To make these constructions, we modified the fill-in of the Hind III site of the BGH-related sequence, described previously, so that only dATP was present in the mixture. This modification added only a single A during fill-in (FIG. 6). We then diluted the reaction mixture 10-fold with S1 buffer (30 mM NaOAc (pH 4.5), 300 mM NaCl, 3 mM $ZnCl_2$), added 2 units/μg DNA of S1 and incubated the mixture at 37° C. for 30 min to cleave off the unfilled DNA overhang (FIG. 6). We then stopped the reaction with phenol and proceeded as before to restrict the DNA fragment with Bam HI and insert it into the desired expression vector. Using these vectors, we observed the following expression levels:

| Deletion | Promoter | Yield of BGH Activity mg/l | BGH-like Molecules/cell |
|---|---|---|---|
| Δ9 | $P_L$ | 100 | $5 \times 10^6$ |

*Again the amino terminal f-Met produced on expression of these constructions could be removed from these BGH-related polypeptides either during expression or subsequent thereto. Because of our experience with the actual amino acid sequence of BGH-Δ9(Ser), we expect that the f-Met is removed either during expression or purification.

We have also used the Δ4 and Δ9 DNA sequences of this invention, as well as a BGH-Δ1 construction prepared by the methods of this invention, under $P_L$ control (with a mu-derived ribosome binding site, as before) to transform various E. coli hosts in order to compare expression levels:

| Deletion | Host[1,2] | Yield[3] |
|---|---|---|
| Δ1 | MC 1061 | $2 \times 10^4$ |
|  | HB 101 | $10 \times 10^4$ |
|  | PR 7 | $30 \times 10^4$ |
| Δ4 | MC 1061 | $3.6 \times 10^5$ |
|  | HB 101 | $6.0 \times 10^6$ |
|  | PR 7 | $13 \times 10^5$ |
| Δ9 | MC 1061 | $1.4 \times 10^6$ |
|  | HB 101 | $1.1 \times 10^6$ |
|  | PR 7 | $1.5 \times 10^6$ |
| Met—Ala—BGH (control) | MC 1061 | $7.5 \times 10^2$ |
|  | PR 7 | $20 \times 10^2$ |

[1]All hosts carried the pcI857 repressor plasmid.
[2]Genotypes of the hosts are as follows:
PR 7: thr leu pnp thi rns mal xal mtl $Sm^R$
HB 101: leu lac pro thi hsr hsm supE recA $Sm^R$
MC 1061: ara leu lac gal hsr hsm StrA
[3]RIA yields in molecules per cell following induction for 2 h at 42° C. in shake flasks.

Therefore, DNA sequences and recombinant DNA molecules characterized by them, having portions of the BGH coding sequence deleted permit the production of bovine growth hormone-like polypeptides in high yield: at least 100 times higher than DNA sequences coding for mature bovine growth hormones in the same expression vectors and hosts, and preferably 1000 times higher. Moreover, such deletions permit the expression of novel bovine growth hormone-like polypeptides, useful after purification using conventional methods, as general anabolic agents in cattle, most especially to increase the rate of growth, weight gain and meat production in those animals. For example, after purification to about 90% homogeneity, the Δ9-BGH produced by our most preferred strain E. coli MC 1061 ($P_L$-mu-Δ9-BGH) displayed about 80% of the growth promoting of native BGH in standard rat tibia assays.

The actual extent of the amino terminal deletion in the DNA sequences of our invention is not critical to our invention and the high yield of the novel BGH-like polypeptides attained by this invention, because the extent of the deletion may depend on the expression control sequence or host used. Instead, the amino terminal deletion should be sufficient to permit the DNA sequence to produce at least about 100 times more molecules/cell of a BGH-like polypeptide, and more preferably at least about 1000 times more, than is produced by the DNA sequence encoding mature BGH in a particular host and expression vector. Such DNA sequences and assays may be constructed by those of skill in the art by following the teachings and examples of this invention. Therefore, such DNA sequences, the recombinant DNA molecules containing them, and the bovine growth hormone-like polypeptides made by them are part of this invention.

The actual method employed to effect the deletions of our invention is also not critical. For example, while we have described an embodiment wherein the deletion was effected using Bal 31 and selected by choosing deletions ending with a T, other deletion methods are also useful in our invention. Such methods include cleaving the BGH coding sequence and replacing a part of the cleaved sequence with a synthetic fragment, Bal 31 digestion and selecting for deletions other than those ending in T, combinations of the two methods, or other deletion methods known in the art.

It should of course be understood that other hosts and expression vectors may also be used to express the novel DNA sequences of this invention and to produce the novel polypeptides of this invention in high yield. Such hosts include other strains of E. coli, as well as strains of Pseudomonas, Streptomyces, Bacillus, yeasts and other fungi, and plant and animal cells in culture. Streptomyces is a particularly preferred host. To express the DNA sequences of this invention in these hosts, the DNA sequences are inserted into expression vectors compatible with the particular host selected and those vectors employed as described above.

Microorganisms and recombinant DNA molecules prepared by the processes of this invention are exemplified by cultures deposited in the American Type Culture Collection, Rockville, Md. on Aug. 16, 1982, and identified there as BGH-A to C.

A. *E. coli* K12 λ (pBGH-(Met-Ala))
B. *E. coli* K12 λ (pBGH-Δ4(Ser))
C. *E. coli* K12 λ (pBGH-Δ9(Ser)).

These cultures were assigned accession numbers 39173, 39174 and 39175, respectively.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. A process for increasing the yield of a bovine growth hormone-like polypeptide to at least 100 times that of a bovine growth hormone-like polypeptide encoded by a DNA sequence of the formula:

```
ATGGCCTTCCCAGCCATGTCCTTGTCCGGC
     CTGTTTGCCAACGCTGTGCTCCGGG
  CTCAGCACCTGCACCAGCTGGCTGCTGAC
 ACCTTCAAAGAGTTTGAGCGCACCTACATC
 CCGGAGGGACAGAGATACTCCATCCAGAACA
    CCCAGGTTGCCTTCTGCTTCTCTGAAAC
   CATCCCGGCCCCCACGGGCAAGAATGAGG
    CCCAGCAGAAATCAGACTTGGAGCTGCTTC
    GCATCTCACTGCTCCTCATCCAGTCGTGG
   CTTGGGCCCCTGCAGTTTCTCAGCAGAGTC
   TTCACCAACAGCTTGGTGTTTGGCACCTC
   GGACCGTGTCTATGAGAAGCTGAAGGACCT
  GGAGGAAGGCATCTTGGCCCTGATGCGGGA
   GGTGGAAGATGGCACCCCCCGGGCTGGGC
    AGATCCTCAAGCAGACCTATGACAAATTTG
    ACACAAACATGCGCAGTGACGACGCGCTG
```

```
     CTCAAGAACTACGGTCTGCTCTCCTGCTTC
       CGGAAGGACCTGCATAAGACGGAGACGTA
      CCTGAGGGTCATGAAGTGCCGCCGCTTCGG
              GGAGGCCAGCTGTGCCTTC
``` in the same vector-host expression system, said process comprising the step of culturing a host transformed with a recombinant DNA molecule comprising DNA sequence encoding a Met Δ or Δ bovine growth hormone-like polypeptide operatively linked to an expression control sequence, said Δ being an amino terminal deletion from the amino acid sequence of mature bovine growth hormone.

2. The process of claim 1, characterized in that said DNA sequence encoding the Met Δ or Δ bovine growth hormone-like polypeptide encodes a polypeptide selected from the group consisting of MetPhe-AA$_3$ to AA$_{191}$ of BGH, Phe-AA$_3$ to AA$_{191}$ of BGH, MetSerLeu-AA$_6$ to AA$_{191}$ of BGH, SerLeu-AA$_6$ to AA$_{191}$ of BGH, MetLeu-AA$_6$ to AA$_{191}$ of BGH, Leu-AA$_6$ to AA$_{191}$ of BGH, MetSer-AA$_{10}$ to AA$_{191}$ of BGH, Ser-AA$_{10}$ to AA$_{191}$ of BGH, Met-AA$_{10}$ to AA$_{191}$ of BGH and AA$_{10}$ to AA$_{191}$ of BGH.

3. The process of claim 1 or 2, characterized in that said DNA sequence encoding the Met Δ or Δ bovine growth hormone-like polypeptide increases the yield of a bovine growth hormone-like polypeptide to at least 1000 times that of a bovine growth hormone-like polypeptide encoded by a DNA sequence of the formula:

```
ATGGCCTTCCCAGCCATGTCCTTGTCCGGCCTGTTTGCCAACGCTGTGCTCCGG
GCTCAGCACCTGCACCAGCTGGCTGCTGACACCTTCAAAGAGTTTGAGCGCACCTACA
TCCCGGAGGGACAGAGATACTCCATCCAGAACACCCAGGTTGCCTTCTGCTTCTCTGA
AACCATCCCGGCCCCCACGGGCAAGAATGAGGCCCAGCAGAAATCAGACTTGGAGCTG
CTTCGCATCTCACTGCTCCTCATCCAGTCGTGGCTTGGGCCCCTGCAGTTTCTCAGCA
GAGTCTTCACCAACAGCTTGGTGTTTGGCACCTCGGACCGTGTCTATGAGAAGCTGAA
GGACCTGGAGGAAGGCATCTTGGCCCTGATGCGGGAGGTGGAAGATGGCACCCCCCGG
GCTGGGCAGATCCTCAAGCAGACCTATGACAAATTTGACACAAACATGCGCAGTGACG
ACGCGCTGCTCAAGAACTACGGTCTGCTCTCCTGCTTCCGGAAGGACCTGCATAAGAC
GGAGACGTACCTGAGGGTCATGAAGTGCCGCCGCTTCGGGGAGGCCAGCTGTGCCTTC
``` in the same vector-host expression system.

4. The process of claim 1 or 2, characterized in that said bovine growth hormone-like polypeptide is selected from the group consisting of polypeptides of the formulae: MetPhe-AA$_3$ to AA$_{191}$ of BGH, Phe-AA$_3$ to AA$_{191}$ of BGH, MetSerLeu-AA$_6$ to AA$_{191}$ of BGH, SerLeu-AA$_6$ to AA$_{191}$ of BGH, MetLeu-AA$_6$ to AA$_{191}$ of BGH, Leu-AA$_6$ to AA$_{191}$ of BGH, MetSer-AA$_{10}$ to AA$_{191}$ of BGH, Ser-AA$_{10}$ to AA$_{191}$ of BGH, Met-AA$_{10}$ to AA$_{191}$ of BGH and AA$_{10}$ to AA$_{191}$ of BGH.

5. The process of claim 1 or 2, wherein said recombinant DNA molecule comprises a DNA sequence encoding a Met Δ or Δ bovine growth hormone-like polypeptide operatively linked to an expression control sequence, said Δ being an amino terminal deletion from the amino acid sequence of mature bovine growth hormone other than a Δ1 deletion or a Δ4 deletion and said DNA sequence increasing the yield of said Met Δ or Δ bovine growth hormone-like polypeptide to at least 100 times that of a bovine growth hormone-like polypeptide encoded by a DNA sequence of the formula:

```
ATGGCCTTCCCAGCCATGTCCTTGTCCGGCCTGTTTGCCAACGCTGTG[TG]CTCCGGG
CTCAGCACCTGCACCAGCTGGCTGCTGACACCTTCAAAGAGTTTGAGCGCACCTACATC
CCGGAGGGACAGAGATACTCCATCCAGAACACCCAGGTTGCCTTCTGCTTCTCTGAAAC
CATCCCGGCCCCCACGGGCAAGAATGAGGCCCAGCAGAAATCAGACTTGGAGCTGCTTC
GCATCTCACTGCTCCTCATCCAGTCGTGGCTTGGGCCCCTGCAGTTTCTCAGCAGAGTC
TTCACCAACAGCTTGGTGTTTGGCACCTCGGACCGTGTCTATGAGAAGCTGAAGGACCT
GGAGGAAGGCATCTTGGCCCTGATGCGGGAGGTGGAAGATGGCACCCCCCGGGCTGGGC
AGATCCTCAAGCAGACCTATGACAAATTTGACACAAACATGCGCAGTGACGACGCGCTG
CTCAAGAACTACGGTCTGCTCTCCTGCTTCCGGAAGGACCTGCATAAGACGGAGACGTA
CCTGAGGGTCATGAAGTGCCGCCGCTTCGGGGAGGCCAGCTGTGCCTTC
``` in the same vector-host expression system.

6. The process of claim 5, characterized in that the expression control sequence is selected from the group consisting of the lac system, the trp system, the major operator and promoter regions of phage λ, the control region of fd coat protein, other sequences known to control the expression of genes of prokaryotic or eukaryotic cells and their viruses and combinations thereof.

* * * * *

UNITED STATES PATENT AND TRADEMARK OFFICE
CERTIFICATE OF CORRECTION

PATENT NO. : 4,693,973

DATED : September 15, 1987

INVENTOR(S) : Gary N. Buell

It is certified that error appears in the above-identified patent and that said Letters Patent is hereby corrected as shown below:

Column 10, line 47, "Friers" should be -- Fiers --.

Column 11, line 7, above "Activity", insert -- Yield of BGH --.

Column 12, line 60, "als" should be -- also --.

Column 14, line 51, "[TG]" should be deleted from the first line of the nucleotide sequence.

Signed and Sealed this

Twenty-second Day of March, 1988

Attest:

DONALD J. QUIGG

Attesting Officer

Commissioner of Patents and Trademarks